United States Patent [19]

Zichis

[11] 3,959,456

[45] May 25, 1976

[54] DIAGNOSTIC SLIDE TEST FOR INFECTIOUS MONONUCLEOSIS

[75] Inventor: Joseph Zichis, Chicago, Ill.

[73] Assignee: Beckman Instruments, Inc., Fullerton, Calif.

[22] Filed: June 20, 1974

[21] Appl. No.: 481,146

Related U.S. Application Data

[60] Division of Ser. No. 112,062, Feb. 2, 1971, Pat. No. 3,826,821, which is a continuation-in-part of Ser. No. 583,433, Sept. 30, 1966, abandoned.

[52] U.S. Cl. .............................. 424/12; 23/230 B; 424/8
[51] Int. Cl.² ................ G01N 31/00; G01N 31/06; G01N 33/16
[58] Field of Search ............... 424/8, 12; 23/230 B, 23/253 TP

[56] References Cited
UNITED STATES PATENTS 3,666,421   5/1972   Price ............................... 424/12 X
3,828,103   8/1974   Fujita ................................. 424/12

OTHER PUBLICATIONS

Davidsohn, AJCP, Vol. 21, 1951, pp. 1101–1113.
Lee, AJCP, Vol. 49, Jan. 1968, pp. 12–18.

Primary Examiner—Jerome D. Goldberg
Assistant Examiner—A. P. Fagelson
Attorney, Agent, or Firm—Knobbe, Martens, Olson, Hubbard & Bear

[57] ABSTRACT

Sheep or horse blood is specially treated to produce an antigen which is readily agglutinable by heterophil type antibodies present in the patient's serum. This antigen possesses properties of stability, sensitivity and agglutinability which are utilized in a serological diagnostic test for infectious mononucleosis. Two other antigens, prepared from beef blood from guinea pig tissues, are used in the test to differentiate the infectious mononucleosis type antibody from the Forssman type.

10 Claims, No Drawings

DIAGNOSTIC SLIDE TEST FOR INFECTIOUS MONONUCLEOSIS

This is a division of application Ser. No. 112,062, filed Feb. 2, 1971, entitled "Method and Reagents for the Diagnosis of Infectious Mononucleosis", now U.S. Pat. No. 3,826,821 which, in turn, is a continuation-in-part of application Ser. No. 583,433, filed Sept. 30, 1966, now abandoned to which priority is claimed.

DESCRIPTION OF THE INVENTION

This invention relates to the provision of a diagnostic test for infectious mononucleosis, and more particularly, to a process for preparing reagents for use in the test and the method of performing the test.

Infectious mononucleosis is a disease of unknown etiology. It has previously been discovered that in the course of this illness the patient develops a heterophil antibody in his serum which is different from the Forssman type heterophil antibodies.[1] Since the latter are known to occur in many normal individuals, and in various disease conditions, and because the heterophil antibodies of infectious mononucleosis and Forssman type antibodies possess certain common characteristics (e.g. they both react with antigens not associated with their production and both types agglutinate sheep and horse erythrocytes[2]), it has been recognized that laboratory diagnostic tests for infectious mononucleosis must be capable of distinguishing between the two.

[1] Paul, J. R. and Bunnell, W. W., Am. J. Med. Sci. 183:90, 1932 Bailey, G. H. and Raffel, S., J. Clin. Investigation, 14:228, 1935
[2] Barrett, A. M., J. Hyg., 41;330, 1941 Hoff, G. and Bauer, S., J.A.M.A., 194:351, 1965

One widely used test (known as the Davidsohn test[3]) employs raw, washed sheep erythrocytes in a presumptive test and differentiates the heterophil antibodies by absorption with suspensions of guinea pig kidneys and beef erythrocytes. The test is performed by a tube method. It involves comparative titrations of the absorbed and unabsorbed test serum. The final results are recorded after two hours of incubation. Other methods which have been used employ treated sheep or horse erythrocytes and are performed by the slide technique.[2]

[3] Davidsohn, I., et al., Am. J. Clin. Path., 21:1101, 1951 Davidsohn, I., J.A.M.A., 108:289, 1937

A primary object of the present invention is to provide a technique for diagnosing infectious mononucleosis which includes the preparation and utilization of unique antigens which function to accurately detect and identify the infectious mononucleosis heterophil antibody. Another object is to provide a diagnostic technique in which presumptive and differential tests for this heterophil antibody are combined into a single test making it possible to establish a diagnosis of infectious mononucleosis within just a few minutes time.

Yet another object of this invention is to provide novel diagnostic procedures and reagents which can be routinely employed without the need of elaborate and costly laboratory facilities, and which can provide accurate results in substantially faster time than previously was thought possible.

In carrying out the invention heterophil type antibodies in the patient's serum are detected by reacting the serum with an antigen specially prepared from sheep or horse blood, and the infectious mononucleosis antibody in the patient's serum is identified by means of differential neutralization reactions of the serum with antigens specially prepared from beef blood and from guinea pig tissues, all of which reactions may be readily visually observed (for example by using the glass slide technique). Thus, the invention contemplates detection of the presence of heterophil antibodies in the patient's serum through reaction with a special antigen prepared from sheep or horse blood, and differentiation of the infectious mononucleosis type heterophil antibody from the Forssman type through use of neutralizing antigens specially prepared from beef blood and from guinea pig tissues.

The preparation and standardization of the various special antigens used in the test may be carried out as described below.

Special Antigens From Sheep or Horse Blood and From Beef Blood

The special antigens from sheep or horse blood and from beef blood are prepared by treating citrated sheep, horse, or beef blood with an aqueous solution containing borate ions preferably along with a suitable anti-contaminant which prevents the growth of microorganisms that may affect the antigen and in this sense acts as a preservative, such as sodium azide, and a suitable agent for enhancing the isotonic character of the solution (e.g. sodium chloride). The solution should be isotonic and neutral, i.e. have a pH close to 7. After treatment the mixture is incubated and the sediment, containing the antigen, is separated out.

Various combinations of acids and salts capable of producing borate ions in solution may be used. Thus combinations of a borate salt of an alkali metal, e.g. sodium borate, with an acid such as ascorbic or isoascorbic, acetic or hydrochloric acid have been used successfully. One particularly useful combination is boric acid and sodium hydroxide.

One representative way in which the special antigen from sheep or horse blood may be prepared is as follows:

1. 500 cc. of sheep or horse blood is added to 600 cc. of a water solution containing 3.8% by weight of sodium citrate.
2. To 2000 cc. of distilled water add 18 gms. of C.P. sodium chloride, 44 gms. of sodium borate, 35 gms. of isoascorbic acid, and 5.0 gms. of sodium azide. Then if necessary adjust to pH 7.0, using either sodium borate or isoascorbic acid.
3. Combine the citrated blood of 1. with the mixture of 2. and mix thoroughly.
4. Incubate the mixture at about 37°C. with stirring at intervals (e.g. three tmes a day). Allow settling to take place overnight. Continue until such settling indicates the formation of a white-grayish layer (the antigen). This usually occurs within five to eight days. Allow the antigen formation to continue for about three additional days. The 37°C. temperature is an optimum in the sense that the antigen tends to be destroyed at higher temperatures, while lower temperatures adversely extend the reaction time beyond the preferred time period stated above.
5. After incubation as described in step 4., supernatant the mixture and centrifuge for 30 minutes at 4500 r.p.m. to separate the antigen from the remaining materials such as the hemoglobin, plasma, cell proteins and sodium citrate. Centrifugation produces three layers, a bottom layer of heavy cellular material, a middle layer of the white-grayish material which contains the antigen, and a top layer of supernatant liquid.
6. Discard both the supernatant liquid (top layer) and the heavy cellular material (bottom layer). Wash the middle layer, containing the antigen, with saline solution by centrifugation, once more discarding top and bottom layers and retaining the middle antigen containing layer. Repeat the washing until the supernatant is clear (indicating that the hemoglobin and other -continued 7. separated materials (see step 5. above) have been removed). Usually three washings suffice.
The white-grayish sediment constitutes the special sheep or horse blood antigen. The antigen is taken up in 500 cc. of saline solution, and preserved by adding 0.2% by weight sodium azide.

Where it is desired to use the sodium hydroxide and boric acid combination mentioned previously, step 2. above is replaced by the following, all other steps remaining the same:

To 3000 cc. of distilled water heated to 37°C. add 27.5 gms. of C.P. sodium chloride, 90 gms. of pH acid, 120 cc. of 1 N NaOH, and 7.0 gms. of sodium azide. Adjust to pII 7.0 if necessary.

The antigen from beef blood is prepared following the same procedures described above except that beef blood is used rather than sheep blood.

The resulting sheep or horse blood antigen may be standardized as follows:

1. Make serial dilutions of the antigen in saline solution from one part antigen to two parts saline solution to one part antigen to thirty-two (32) parts saline solution.
2. Place a drop of each dilution on a separate one inch square marked on a glass plate.
3. To each such drop, add a drop of standard positive infectious mononucleosis serum.*
4. Mix the reagents on each square with a separate wooden applicator.
5. Manipulate the glass plate over an indirect light and observe the agglutination reactions.

*A serum collected from a proven case of the disease, and having a 1-160 titer as determined by the Davidsohn test.

The dilution that reacts the fastest and produces the heaviest agglutination constitutes the titer of the antigen. The final antigen then is made up to this dilution.

It is usually found that the antigen prepared from horse blood is somewhat more sensitive than that prepared from sheep blood.

The beef antigen may be standardized by demonstrating its neutralizing effect against a standard positive infectious mononucleosis serum.

Special Antigen From Guinea Pig Tissues

The special antigen from guinea pig tissues is prepared by making a saline extract of guinea pig kidney, spleens and lungs. One technique which may be used is as follows:

1. Grind the guinea pig tissues in an Osterizer or like blender at full speed for five minutes, and make an 18% by weight suspension of tissues in saline solution.
2. Add about 0.2% by weight sodium azide.
3. Store at about 2-5°C. for approximately 24 hours.
4. Centrifuge at 2000 r.p.m. for 15 minutes.
5. Decant and save the supernatant liquid; discard the sediment.
6. Heat the supernatant liquid for 20 minutes at 56°C.
7. Centrifuge again at 2000 r.p.m. for 20 minutes.
8. Decant and save the supernatant liquid which contains the antigen; discard the sediment. If the supernatant liquid is found not to be of sufficient titer, when standardized as described below, it should be concentrated to the desired potency using a suitable evaporation technique. If the supernatant liquid is too concentrated it should be diluted.

The guinea pig antigen may be standardized by testing serial dilutions of it with a Forssman heterophil antiserum or a positive infectious mononucleosis serum as described above. The Forssman antibodies are neutralized (thus agglutination does not occur), and the infectious mononucleosis antibody is not.

Test

The test which results from practice of the invention makes use of the discovery that the specially prepared antigens described above each perform different functions leading to specific detection and identification of the heterophil antibody of infectious mononucleosis. Thus, the specially prepared sheep or horse blood antigen agglutinatively reacts with, and thus detects the presence of, any heterophil type antibody, including both the Forssman and the infectious mononucleosis types. The other two specially prepared antigens then accurately distinguish between the Forssman and the infectious mononucleosis type heterophil antibodies. The specially prepared beef blood antigen functions to inactivate or neutralize the infectious mononucleosis type heterophil antibody but does not neutralize the Forssman type. The specially prepared guinea pig antigen, on the other hand, neutralizes the Forssman type but not the infectious mononucleosis antibody. The manner in which this discovery is utilized will be seen from the below described test procedure.

To perform the test, one drop of the patient's serum is placed in each of three one inch squares on a marked glass plate.

The separately prepared and standardized sheep or horse blood, beef blood and guinea pig tissue antigens are individually thoroughly shaken. Then to the first square on the glass plate a drop of the beef blood antigen is added; to the second square a drop of the guinea pig tissue antigen is added; and to the third square a drop of saline solution is added. To a fourth square two drops of saline solution are added.

Then the reagents in each of the first three squares are mixed with separate wooden applicators and allowed to stand for about one minute.

Next a drop of the special sheep or horse blood antigen is added to each of the four squares. Again the reagents in each square are mixed with the wooden applicators as before.

Finally the glass plate is manipulated gently over an indirect light for not more than about two minutes and the presence or absence of agglutination reactions is visually observed. The final agglutination reading should be made five minutes later.

In a positive test, the heterophil antibody of infectious mononucleosis present in the patient's serum is neutralized or inactivated by the beef blood antigen (in the first square), but not by the guinea pig tissue antigen (in the second square). Thus, when the sheep or horse blood antigen is added to each of the glass squares agglutination does not occur in the presence of the beef blood antigen (first square), but does occur in the presence of the guinea pig tissue antigen (second square). In addition, agglutination also occurs in the third square where the sheep or horse blood antigen reacts with the patient's serum without other antigens being present. The mixture in the fourth square serves to control the granulation that may be present in the sheep or horse blood antigen.

A negative test is manifested in either of two ways, viz. there will be no agglutination of the serum with any of the three antigens (in which case no heterophil antibodies are present), or there will be agglutination of the serum with the sheep or horse blood antigen (third square) and in the presence of the beef blood antigen (first square) but not in the presence of the guinea pig tissue antigen (second square). The latter situation shows the presence of the Forssman type antibodies but not of the infectious mononucleosis type.

In rare cases, agglutination may occur in the presence of all three antigens. Such a reaction may result if the specimen contains both the Forssman and the specific infectious mononucleosis antibodies. It may also result if only one of the two antibodies is present, but its titer is higher than the beef or guinea pig antigens are capable of neutralizing. A differential titration of the specimen will resolve these conditions.

While the types of agglutination that occur in a positive test reaction range from coarse to fine clumping, any detectable agglutination is interpreted as a positive reaction. Since with some sheep or horse blood antigens, a fine granulation of the antigen may occur, the antigen saline control procedure carried out using the fourth glass square serves to distinguish this granulation from the positive reactions given in the test.

Occasionally, the test should be performed with a positive infectious mononucleosis serum, so that the typical and distinct action of the antigens may be observed.

Nineteen hundred (1900) sera from suspected cases of infectious mononucleosis that gave positive agglutination by the Davidsohn presumptive test have been tested according to the present invention utilizing the sheep blood antigen on a comparative basis with the Davidsohn differential method. The presumptive titer of these sera ranged from 1–7 to 1–896.

When these sera were subjected to the Davidsohn differential method eight hundred twenty seven (827) tested positive for infectious mononucleosis, and ten hundred seventy three (1073) tested negative. When the same sera were tested using the method of the present invention, a total of eight hundred thirty three (833) tested positive (including the 827 which were positive according to the Davidsohn test), and ten hundred sixty seven (1067) tested negative.

To confirm the specificity of the method of the present invention, three hundred (300) sera that tested negative according to the Davidsohn presumptive test were tested using the method of the invention and were also found to be negative.

Two hundred and fifteen (215) sera from suspected cases of infectious mononucleosis that tested positively using the sheep blood antigen as described herein, were also tested according to the present invention utilizing the horse blood antigen. All the sera likewise tested positive. The comparative results showed that the horse blood antigen was more sensitive than the sheep blood antigen.

While the invention has been described in conjunction with specific embodiments thereof, it is evident that many alternatives, modifications, and variations will become apparent to those skilled in the art in light of the foregoing description. Accordingly, it is intended to embrace all such alternatives, modifications, and variations as fall within the spirit and broad scope of the appended claims.

I claim as my invention:

1. A serological diagnostic test in which the reactions are carried out on a slide, comprising the steps of:
   a. obtaining human blood serum suspected to contain the heterophil antibody characteristic of infectious mononucleosis;
   b. mixing on a slide an aliquot of said serum with a first antigen which neutralizes without agglutination the Forssman type heterophil antibodies, but not the infectious mononucleosis antibody;
   c. mixing on a slide an aliquot of said serum with a second antigen which neutralizes without agglutination the infectious mononucleosis antibody, but not the Forssman type antibodies;
   d. adding to each of the mixtures resulting from the preceding steps a third antigen prepared from erythrocytes which is free of hemoglobin and which is agglutinative with the unneutralized heterophil type antibodies; and
   e. observing, in the case of a positive test for infectious mononucleosis, occurrence of agglutination on the slide having thereon the serum-antigen mixture containing said first antigen and no agglutination on the slide having thereon the mixture containing said second antigen.

2. The diagnostic slide test of claim 1 wherein the mixtures resulting from step d. are manipulated gently over an indirect light for not more than about two minutes before the observation is made.

3. The diagnostic slide test of claim 1 wherein the second antigen is prepared by treating beef erythrocytes with an isotonic aqueous solution having a pH of about 7 and containing borate ions and a preservative, incubating the resulting mixture of erythrocytes and isotonic solution at about 37°C. for about 5 to about 11 days, and separating the resulting stable serologically active white-grayish antigen from the residual liquid and blood substances.

4. The diagnostic slide test of claim 1 wherein the first antigen is prepared by treating guinea pig tissues with an aqueous saline solution, incubating the resulting mixture at about 2°C. to about 5°C. for about 24 hours, separating the liquid from the residual sediment, maintaining the resulting liquid at about 56°C. for about 15 minutes, and separating the liquid containing the antigen from the residual sediment.

5. The diagnostic slide test of claim 4 wherein the second antigen is prepared by treating beef erythrocytes with an isotonic aqueous solution having a pH of about 7 and and containing borate ions and a perservative, incubating the resulting mixture of erythrocytes and isotonic solution at about 37°C. for about 5 to about 11 days, and separating the resulting stable serologically active white-grayish antigen from the residual liquid and blood substances.

6. The diagnostic slide test of claim 5 wherein the third antigen is prepared by treating sheep or horse erythrocytes with an isotonic aqueous solution having a pH of about 7 and containing borate ions and a preservative, incubating the resulting mixture of erythrocytes and isotonic solution at about 37°C. for about 5 to about 11 days, and separating the resulting stable serologically active white-grayish antigen from the residual liquid and blood substances.

7. The diagnostic slide test of claim 1 wherein the third antigen is prepared by treating sheep erythrocytes with an isotonic aqueous solution having a pH of about 7 and containing borate ions and a preservative, incubating the resulting mixture of erythrocytes and isotonic solution at about 37°C. for about 5 to about 11 days, and separating the resulting stable serologically active white-grayish antigen from the residual liquid and blood substances.

8. The diagnostic slide test of claim 7 wherein the first antigen is prepared by treating guinea pig tissues with an aqueous saline solution, incubating the resulting mixture at about 2°C. to about 5°C. for about 24 hours, separating the liquid from the residual sediment, maintaining the resulting liquid at about 56°C. for about 15 minutes, and separating the liquid containing the antigen from the residual sediment.

9. The diagnostic slide test of claim 1 wherein the third antigen is prepared by treating horse erythrocytes with an isotonic aqueous solution having a pH of about 7 and containing borate ions and a preservative, incubating the resulting mixture of erythrocytes and isotonic solution at about 37°C. for about 5 to about 11 days, and separating the resulting stable serologically active white-grayish antigen from the residual liquid and blood substances.

10. The diagnostic slide test of claim 9 wherein the first antigen is prepared by treating guinea pig tissues with an aqueous saline solution, incubating the resulting mixture at about 2°C. to about 5°C. for about 24 hours, separating the liquid from the residual sediment, maintaining the resulting liquid at about 56°C. for about 15 minutes, and separating the liquid containing the antigen from the residual sediment.

* * * * *

UNITED STATES PATENT OFFICE
CERTIFICATE OF CORRECTION

PATENT NO. : 3,959,456
DATED : May 25, 1976
INVENTOR(S) : Joseph Zichis

It is certified that error appears in the above-identified patent and that said Letters Patent are hereby corrected as shown below:

Column 2, Line 57 - "supernatant" should be --stir--

Column 3, Line 15 - "pH" should be --boric--

Signed and Sealed this

Fourteenth Day of September 1976

[SEAL]

Attest:

RUTH C. MASON
Attesting Officer

C. MARSHALL DANN
Commissioner of Patents and Trademarks